(12) United States Patent
Tischendorf et al.

(10) Patent No.: US 11,872,405 B2
(45) Date of Patent: Jan. 16, 2024

(54) FEEDTHROUGH ASSEMBLY

(71) Applicant: Medtronic, Inc., Minneapolis, MN (US)

(72) Inventors: Brad C. Tischendorf, Minneapolis, MN (US); Andrew J. Thom, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 156 days.

(21) Appl. No.: 17/343,467

(22) Filed: Jun. 9, 2021

(65) Prior Publication Data

US 2021/0290964 A1 Sep. 23, 2021

Related U.S. Application Data

(63) Continuation of application No. 16/786,078, filed on Feb. 10, 2020, now Pat. No. 11,058,883.

(Continued)

(51) Int. Cl.
| | |
|---|---|
| *A61N 1/37* | (2006.01) |
| *A61N 1/375* | (2006.01) |
| *C03C 3/064* | (2006.01) |
| *C03C 3/068* | (2006.01) |
| *C03C 3/066* | (2006.01) |

(Continued)

(52) U.S. Cl.
CPC ............ *A61N 1/3754* (2013.01); *C03C 3/064* (2013.01); *C03C 3/066* (2013.01); *C03C 3/068* (2013.01); *C03C 8/02* (2013.01); *C03C 8/04* (2013.01); *C03C 8/24* (2013.01); *H01B 3/087* (2013.01); *H01B 17/22* (2013.01); *C03C 2205/00* (2013.01)

(58) Field of Classification Search
CPC .............................. A61N 1/754; A61N 1/3754
USPC .......................................................... 174/650
See application file for complete search history.

(56) References Cited

U.S. PATENT DOCUMENTS

| | | | |
|---|---|---|---|
| 4,940,858 | A | 7/1990 | Taylor et al. |
| 5,175,067 | A | 12/1992 | Taylor et al. |

(Continued)

FOREIGN PATENT DOCUMENTS

| | | | |
|---|---|---|---|
| DE | 3918691 | * | 6/1989 |
| EP | 2007689 A2 | | 12/2008 |

(Continued)

OTHER PUBLICATIONS

Rosenflanz et al., "Bulk glasses and ultrahard nanoceramics based on alumina and rare-earth oxides", Nature, vol. 430, Aug. 12, 2004, pp. 761-764.

(Continued)

*Primary Examiner* — Stanley Tso
(74) *Attorney, Agent, or Firm* — Mueting Raasch Group

(57) ABSTRACT

A feedthrough assembly includes: a ferrule; an insulating structure; and a seal fixedly securing the insulating structure within the ferrule, the seal comprising a glass and single-phase particulate dispersed therein; wherein the glass includes: 25% to 40% $B_2O_3$; 0 to 25% CaO; 0 to 25% MgO; 0 to 25% SrO; 0 to 10% $La_2O_3$; 5% to 15% $SiO_2$; and 10% to 20% $Al_2O_3$; wherein all percentages are mole percentages of the glass.

10 Claims, 4 Drawing Sheets

Related U.S. Application Data

(60) Provisional application No. 62/806,107, filed on Feb. 15, 2019.

(51) Int. Cl.

| | |
|---|---|
| *C03C 8/24* | (2006.01) |
| *C03C 8/04* | (2006.01) |
| *H01B 3/08* | (2006.01) |
| *H01B 17/22* | (2006.01) |
| *C03C 8/02* | (2006.01) |

(56) References Cited

U.S. PATENT DOCUMENTS

| | | | |
|---|---|---|---|
| 5,306,581 A | 4/1994 | Taylor et al. | |
| 5,902,326 A | 5/1999 | Lessar et al. | |
| 6,855,456 B2 | 2/2005 | Taylor et al. | |
| 3,288,654 A1 | 10/2012 | Taylor et al. | |
| 9,643,020 B2 | 5/2017 | Goldman et al. | |
| 2006/0247714 A1 | 11/2006 | Taylor et al. | |
| 2008/0296753 A1 | 12/2008 | Carter | |
| 2009/0229858 A1 | 9/2009 | Taylor et al. | |
| 2009/0321107 A1* | 12/2009 | Taylor | H01M 50/191 174/137 R |
| 2011/0108320 A1 | 5/2011 | Lakner et al. | |
| 2014/0042891 A1* | 2/2014 | Furukubo | C03C 10/16 252/582 |
| 2018/0304084 A1 | 10/2018 | Stevenson et al. | |
| 2019/0127266 A1 | 5/2019 | Hirose | |
| 2019/0182962 A1* | 6/2019 | Gong | C23C 18/1245 |

FOREIGN PATENT DOCUMENTS

| | | |
|---|---|---|
| WO | 2011/031725 | 3/2011 |
| WO | 2017/183490 | 10/2017 |

OTHER PUBLICATIONS

Dume, "Glass breakthrough", Physics World, Aug. 11, 2004.

Liu et al., "Influence of alumina additions on the physical and chemical properties of lithium-iron-phosphate glasses", Science Direct, Jul. 2013.

* cited by examiner

FEEDTHROUGH ASSEMBLY

CONTINUING APPLICATION DATA

This application is a continuation of U.S. application Ser. No. 16/786,078, filed Feb. 10, 2020, which claims the benefit of U.S. Provisional Application Ser. No. 62/806,107, filed Feb. 15, 2019, which are incorporated by reference herein.

FIELD

The present technology is generally related to feedthrough assemblies for use in implantable medical devices, and more particularly to glass seals within the feedthrough assemblies, wherein the glass seals include a glass and single-phase particulate dispersed therein.

BACKGROUND

Numerous devices (e.g., implantable medical devices (IMDs)), electrochemical cells (e.g., batteries, capacitors, or sensors) are hermetically sealed to prevent liquid from contacting electronic components within the device. A typical feedthrough assembly includes a conductive element (e.g., wires or pins), a ferrule or sleeve member, an insulating member (e.g., glass, ceramic), and a seal. Feedthroughs include those described in U.S. Pat. Nos. 6,855,456 and 5,175,067 and U.S. Pat. App. Pub. No. 2006/0247714, all to Taylor et al. The ferrule or sleeve member includes an aperture configured to receive the insulating member. A seal may be located between the ferrule or sleeve member and the insulating member. Insulating members include those formed of Ta-23 glass and Cabal-12 glass, as described in U.S. Pat. No. 5,306,581 to Taylor et al. An exemplary feedthrough assembly may be inserted, for example, into a housing of a battery such that a portion of the conductive element extends into the housing to connect with battery elements while another portion of the conductive element extends outside of the housing to connect with other electronic components.

It is desirable to develop improved feedthroughs for IMDs, particularly those that include an insulating member made of a material that can be readily adjusted to possess mechanical properties as needed for the application.

SUMMARY

The present disclosure provides a feedthrough assembly that includes: a ferrule; an insulating structure; and a glass seal fixedly securing the insulating structure within the ferrule, the glass seal (e.g., a first glass seal) including a glass and single-phase particulate dispersed therein (i.e., a filled glass).

The glass of the glass seal includes (nominally): 25% to 40% $B_2O_3$; 0 to 25% CaO; 0 to 25% MgO; 0 to 25% SrO; 0 to 10% $La_2O_3$; 5% to 15% $SiO_2$; and 10% to 20% $Al_2O_3$; wherein all percentages are mole percentages of the glass (and all component percentages add up to 100%).

In certain embodiments, the single-phase particulate of the glass seal includes $Al_2O_3$, $Y_2O_3$, $ZrO_2$, $TiO_2$, MgO, ZnO, BaO, CaO, $Nb_2O_5$, $Ta_2O_5$, SiC, $Si_3N_4$, or mixtures thereof.

In certain embodiments, the feedthrough assembly further includes at least one terminal pin, wherein the insulating structure includes a top portion, a bottom portion, and an inner diameter portion, wherein the inner diameter portion defines at least one aperture extending from the top portion to the bottom portion, and wherein the at least one terminal pin extends through the at least one aperture. In certain embodiments, the feedthrough assembly further includes a gold braze sealing the at least one terminal pin with the insulating structure. Alternatively, in certain embodiments, the feedthrough assembly further includes a glass seal (e.g., a second glass seal) sealing the at least one terminal pin with the insulating structure. In certain embodiments, this second glass seal includes the filled glass described herein.

In certain embodiments, the present disclosure provides a feedthrough assembly, including: a ferrule; an insulating structure comprising a top portion, a bottom portion, and an inner diameter portion, wherein the inner diameter portion defines at least one aperture extending from the top portion to the bottom portion; at least one terminal pin extending through the at least one aperture; and a glass seal fixedly securing the at least one terminal pin with the insulating structure. The glass seal includes a glass and single-phase particulate dispersed therein; wherein the glass includes: 25% to 40% $B_2O_3$; 0 to 25% CaO; 0 to 25% MgO; 0 to 25% SrO; 0 to 10% $La_2O_3$; 5% to 15% $SiO_2$; and 10% to 20% $Al_2O_3$; wherein all percentages are mole percentages of the glass.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the disclosure that may afford certain benefits, under certain circumstances. However, other claims may also be preferred, under the same or other circumstances. Furthermore, the recitation of one or more preferred claims does not imply that other claims are not useful, and is not intended to exclude other claims from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "includes at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.) and any sub-ranges (e.g., 1 to 5 includes 1 to 4, 1 to 3, 2 to 4, etc.).

The term "in the range" or "within a range" (and similar statements) includes the endpoints of the stated range.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

BRIEF DESCRIPTION OF DRAWINGS

Exemplary embodiments will now be described more fully with reference to the accompanying drawings.

DETAILED DESCRIPTION

The present disclosure provides a feedthrough assembly in a medical device, such as used in a microelectromechanical system (MEMS) package. The conductive hermetic feedthrough connects an interior cavity in the MEMS device to another electronic component or device (e.g., lead interconnect) outside of the MEMS package. The MEMS package may be hermetic and isolated from body fluid contact more so than packages that employ an epoxy attachment to a silicon substrate.

Figure 1:
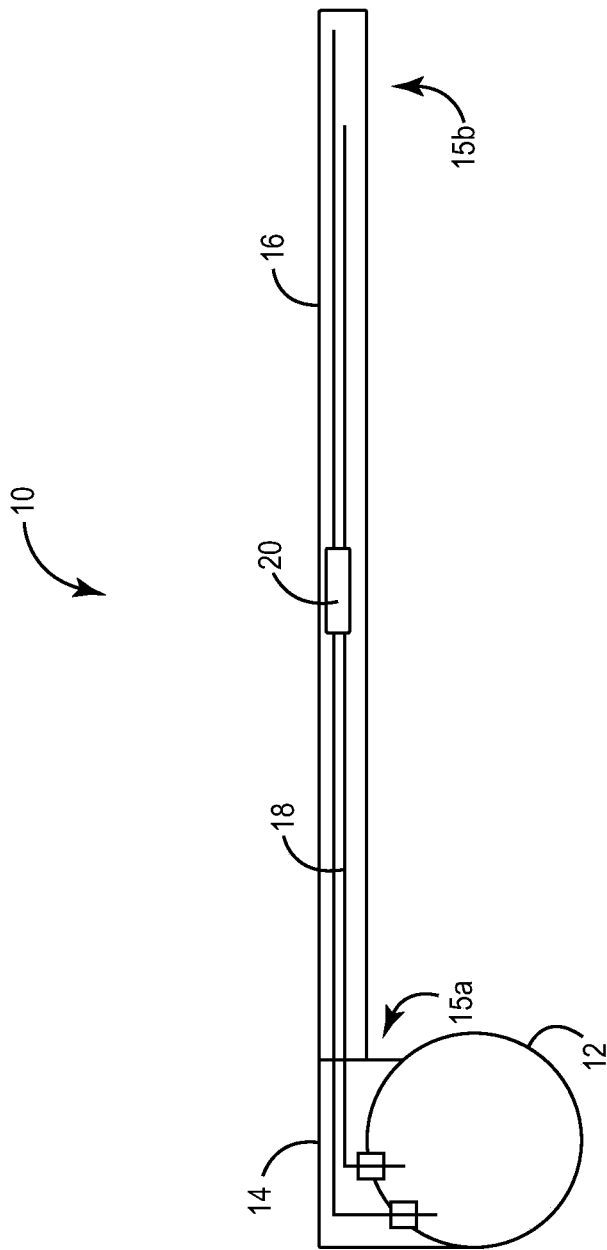
FIG. 1 depicts a schematic view of an implantable medical device.

FIG. 1 depicts a functional unit 20 in a medical device system 10. Functional unit 20 includes a feedthrough assembly (not shown) on or in an integrated circuit (IC), a substrate that includes electronic components (e.g., transistors, logic gates, switches), or a substrate alone. Functional unit 20 can be used anywhere outside the medical device housing 12 and may be electrically connected to one or more conductor(s) 18. For example, functional unit 20 can serve as a sensor (e.g., pressure sensor) that employs a feedthrough assembly.

Medical device system 10 includes a medical device housing 12 having a connector module 14 that electrically couples various internal electrical components of medical device housing 12 to a proximal end 15a of a medical lead 16 such as one or more conductors 18 (e.g., coil, wire) that extend to a distal end 15b of lead 16. Medical device system 10 may include any of a wide variety of medical devices that include one or more medical lead(s) 16 and circuitry coupled to the medical lead(s) 16. By way of example, medical device system 10 may take the form of an implantable cardiac pacemaker that provides therapeutic stimulation to the heart or a neurostimulator. Alternatively, medical device system 10 may take the form of an implantable cardioverter, an implantable defibrillator, an implantable cardiac pacemaker-cardioverter-defibrillator (PCD), an implantable pulse generator, or an implantable medical device that solely monitors conditions associated with the patient.

Figure 2:
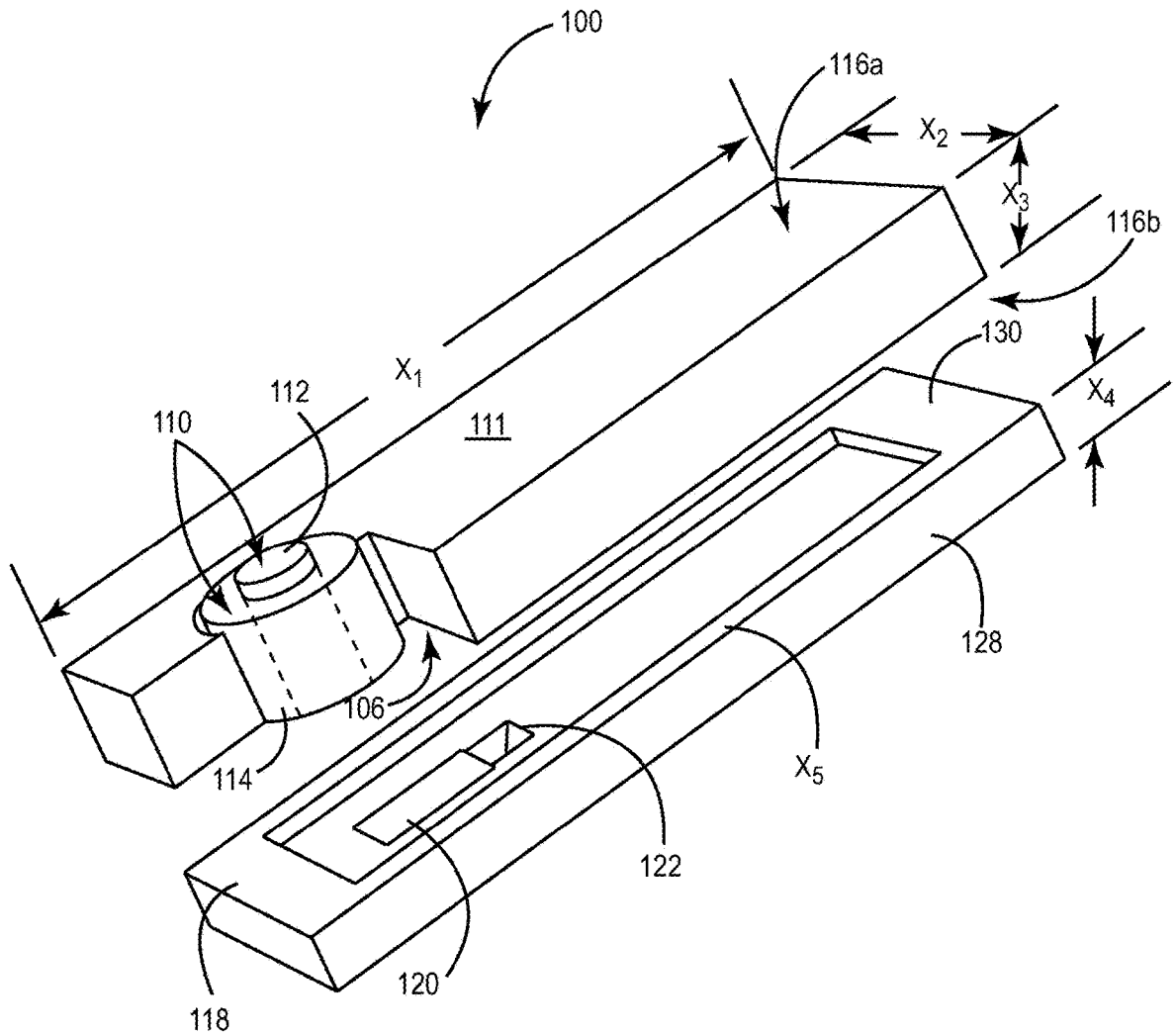
FIG. 2 is a schematic cut away view of a MEMS package that includes a feedthrough assembly.

FIG. 2 illustrates one embodiment of a MEMS package 100 for medical device system 10 (FIG. 1). MEMS package 100, in one embodiment, may be used in or for a sensor. For example, a MEMS package 100 could be associated with a transducer, which converts a signal into an electrical signal (i.e., voltage, current).

MEMS package 100 includes a feedthrough assembly 110, a first substrate 111, and a second substrate 128. Feedthrough assembly 110 may be hermetically disposed in an aperture 106 of first substrate 111, and coupled to second substrate 128. Feedthrough assembly 110 (e.g., glass-pin-insulator seal) includes a conductive element 112 (e.g., pin) hermetically housed in an insulating member 114 (also referred to as sealing glass or glass seal). Conductive element 112 may be formed of a conductive material, such as tantalum (Ta), niobium (Nb), titanium (Ti), platinum (Pt), iridium (Ir) and/or alloys thereof.

Insulating member 114 may include a glass. Typical glass for formation of insulating member 114 includes boro-alumino, boro-alumino silicate and/or boro silicate type glasses with a wide range of thermal expansions to approximately match biostable conductive element 112 materials such as Ta, Nb, niobium-titanium (Nb—Ti) alloy, Pt, Pt alloys, Ti, and alloys of Ti and/or other suitable materials. The element(s) and/or compounds used to form insulating member 114 are selected in a manner to reduce tensile stresses with conductive element 112. For example, insulating member 114, employing glass, has a coefficient of thermal expansion (CTE) value equivalent to or within 15% of the CTE associated with conductive element 110.

The insulating member 114 may be formed from a glass preform. For example, in making a feedthrough assembly 110, the glass preform may be melted so that the molten glass engages conductive element 112 and the inner walls of aperture 106 and subsequently cooled to form insulating member 114.

The glass preform (and the resultant glass seal) described herein includes a filled glass composition. The filled glass composition includes a glass and a single-phase particulate dispersed therein. There may be more than one glass seal, and hence, more than one filled glass composition. Reference to a first glass seal, first glass, or first single-phase particulate, for example, does not necessarily require that there be a second glass seal, glass, or particulate.

In certain embodiments, the glass of the filled glass composition includes 25-40% $B_2O_3$, 0-25% CaO, 0-25% MgO, 0-25% SrO, 0-10% $La_2O_3$ (preferably, greater than 0%), 5-15% $SiO_2$, and 10-20% $Al_2O_3$, where all percentages represent mole percents of the glass (and all component percentages add up to 100%).

In certain embodiments, the glass of the filled glass composition includes 30-40% $B_2O_3$, 0-20% CaO, 0-20% MgO, 0-20% SrO, 0-5% $La_2O_3$ (preferably greater than 0%), 5-10% $SiO_2$, and 10-20% $Al_2O_3$, where all percentages represent mole percents of the glass (and all component percentages add up to 100%).

In certain embodiments, the glass of the filled glass composition includes at least one of CaO, MgO, or SrO. In certain embodiments, the glass of the filled glass composition includes a mixture of two or more of CaO, MgO, or SrO. In certain embodiments, the glass of the filled glass composition includes a mixture of CaO and MgO.

In certain embodiments, the glass of the filled glass composition includes 25-35% $B_2O_3$, 15-25% CaO, 15-25% MgO, 3-7% $La_2O_3$, 5-15% $SiO_2$, and 10-20% $Al_2O_3$, where all percentages represent mole percents of the glass (and all component percentages add up to 100%).

In some embodiments, the glass of the filled glass composition includes up to 10% of $MnO_2$, and in some cases the $MnO_2$ may be 15%.

In some embodiments, all or some of the amounts of CaO and/or MgO are replaced with a corresponding amount of SrO. For example, 10% of CaO and 5% MgO may be replaced with 15% SrO. However, the amounts of CaO and MgO are not entirely replaced by SrO, and none of CaO, MgO, and SrO is above 25% (or above 20%).

In some embodiments, the glass includes 30% to 50% of a member selected from the group consisting of CaO, MgO, and SrO, and combinations thereof, with the proviso that the individual amounts of CaO, MgO, and SrO are each not greater than 25% (or not greater than 20%).

In some embodiments, the glass includes 30% to 50% of a member selected from the group consisting of CaO, MgO, and combinations thereof, with the proviso that the individual amounts of CaO and MgO are each not greater than 25% (or not greater than 20%).

In some embodiments, the glass includes 30% $B_2O_3$, 5% $La_2O_3$, 10% $SiO_2$, and 15% $Al_2O_3$, and 30% to 50% of a member selected from the group consisting of CaO, MgO, and combinations thereof, with the proviso that the individual amounts of CaO and MgO are each not greater than 25% (or not greater than 20%).

In some embodiments, the glass composition includes 30% $B_2O_3$, 20% CaO, 20% MgO, 5% $La_2O_3$, 10% $SiO_2$, and 15% $Al_2O_3$.

The glass material can be made using well-known techniques of forming glasses.

The filled glass composition includes single-phase particulate. In this context "single-phase" means a chemically homogeneous material that is composed of two or more elements and possesses a characteristic crystallographic structure.

Examples of single-phase particulate includes $Al_2O_3$, $Y_2O_3$, $ZrO_2$, $TiO_2$, MgO, ZnO, BaO, CaO, $Nb_2O_5$, $Ta_2O_5$, SiC, $Si_3N_4$, or mixtures thereof.

The type and amount of single-phase particulate may be selected to provide desirable physical properties without impacting the chemistry of the glass. Examples of such physical properties include thermal expansion, elastic modulus, and fracture toughness. Depending on the particulate selected, and the amount used, such physical properties can be tailored to meet the requirements of use.

For example, to obtain a robust seal in an electrical feedthrough, the residual stress state of the seal must be carefully considered. To best use the filled glass described herein as a seal material with a niobium pin and titanium ferrule, it is desirable to reduce the coefficient of thermal expansion (CTE) of the glass. This can be accomplished, for example, by adding alumina to the glass since alumina has a lower CTE compared to the glass. For example, the CTE values of alumina and a specific embodiment of the glass described herein (30% $B_2O_3$, 20% CaO, 20% MgO, 5% $La_2O_3$, 10% $SiO_2$, and 15% $Al_2O_3$) are 7.66 and 8.77 µm/m/° C., respectively, from 25° C. to 630° C. The elastic modulus of the glass increases with the addition of alumina due to the higher modulus value of alumina.

Table 1 shows exemplary values of CTE and Elastic Modulus for an alumina-filled glass (30% $B_2O_3$, 20% CaO, 20% MgO, 5% $La_2O_3$, 10% $SiO_2$, and 15% $Al_2O_3$) for alumina additions up to 25%. The properties reported in Table 1 were measured on bulk shapes made from melted mixtures of the glass and alumina which naturally include a small amount of porosity. CTE is approximately independent of small amounts of porosity, while elastic modulus is known to decrease with porosity. The samples contained 4.2% porosity, which is contained only in the glass portion of the seal; this porosity reduces elastic modulus of the glass-alumina composite material.

These modified properties eliminate undesirable tensile stresses at the glass-pin interface for additions as small as 3 wt-% alumina. Seals with these filled glass compositions have been produced and shown to have desirable robustness for a titanium-based ferrules and a niobium-based pins. As the alumina loading increases, fracture resistance of the modified glass also increases, and this is highly desirable for improved mechanical robustness of the seal to loading on the pin. Fracture toughness of a specific embodiment of the glass described herein is 1.0 MPa-m$^{0.5}$ and increases to 1.6 MPa-m$^{0.5}$ for additions of 10 wt-% to 20 wt-% alumina to the glass.

TABLE 1

| Alumina content (wt-%) | $CTE_{25°-630° C.}$ (μm/m/° C.) | Elastic Modulus (GPa) |
|---|---|---|
| 0 | 8.77 | 94.0 |
| 5 | 8.64 | 103.1 |
| 10 | 8.52 | 112.3 |
| 15 | 8.42 | 121.5 |
| 20 | 8.34 | 130.6 |
| 25 | 8.26 | 139.8 |

In certain embodiments, the average particle size of such single-phase particulate is typically no greater than 10 micrometers (i.e., microns). In certain embodiments, the average particle size of such particulate is typically no greater than 5 microns. In certain embodiments, the average particle size of such particulate is typically at least 1 micron.

The shape of the single-phase particulate may be any of a variety of shapes, but typically not needle-like.

In certain embodiments, the single-phase particulate is used in an amount of least 1 wt-%, based on the total weight of the glass and particulate. In certain embodiments, the single-phase particulate is used in an amount of least 2 wt-%, at least 3 wt-%, at least 5 wt-%, and at least 10 wt-%, based on the total weight of the glass and particulate. In certain embodiments, the single-phase particulate is used in an amount of up to 25 wt-%, based on the total weight of the glass and particulate. In certain embodiments, the single-phase particulate is used in an amount of up to 20 wt-%, based on the total weight of the glass and particulate. For example, in certain embodiments, the single-phase particulate is used in an amount of 3 wt-%, 5 wt-%, 10 wt-%, 13 wt-%, 15 wt-%, 16 wt-%, or 20 wt-%, based on the total weight of the glass and particulate.

The filled glass material may be made using a variety of well-known techniques. For example, the glass material can be reduced to powder form by ball milling and then sieved to a suitable particle size classification for powder processing. Single-phase particulate powder (e.g., alumina powder) can be purchased from various vendors having high purity and pre-sieved to a suitable particle size classification for mixing with the glass powder. The desired amounts of glass and single-phase particulate (e.g., alumina) powders are typically blended and then thoroughly mixed in a ball mill. A bulk shape can be made by packing the mixed powder in a nonreactive tube, such as graphite, and then heated to above the glass transition temperature of the glass in an inert atmosphere, such as argon. The glass powder reflows to form a continuous glassy matrix with minimal porosity and with the particulate distributed throughout the glass. The reflow temperature is set to ensure there is no reaction between the particulate and the glass. This general method can be extended to produce more complex shapes, such as cylinders, of the filled glass for use as the electrical feedthrough insulators.

The filled glass of the present disclosure is not a glass ceramic. In glass ceramics, the particulate is precipitated out of solution (as opposed to a preformed particulate that is premixed with glass powder). Accordingly, the particulate may be in the form of needles in a glass ceramic.

Various components of the filled glass composition provide benefits in making a feedthrough assembly 110 (FIG. 2) and provide the resulting insulating member 114 with advantageous properties. In particular, $La_2O_3$ provides for better glass flow in melting and forming the insulating member 114, as lower temperatures may be employed compared to glass without $La_2O_3$ or with less $La_2O_3$. Lanthanum oxide also increases the coefficient of thermal expansion (CTE) value of the glass. For example, glass with little or no lanthanum oxide may have a CTE of 6.5, where glass with lanthanum oxide as described herein may have a CTE of 8.0. The increased CTE values are closer to the CTE values for metals, such as niobium (Nb), titanium (Ti), platinum (Pt), iridium (Ir) and/or alloys thereof. Similar CTE values alter the resulting compressive force applied to the glass insulating member when disposed within a ferrule (not shown) or the inner walls of aperture 106 upon forming and cooling the feedthrough assembly 110. Excessive tensile force can be caused by this alteration, which can cause tensile cracks in the glass insulating member 114. The propensity for such tensile cracks may be reduced by employing the present compositions. For example, the present compositions may provide CTE values that are 10-15% less than the metal of the inner walls of aperture 106 or of a ferrule.

Strontium oxide within the glass composition also lowers the processing temperature. For example, as described above, all or some of the amounts of CaO and/or MgO may be replaced with a corresponding amount of SrO. In this way, the processing temperature of the glass composition may be adjusted, for example, in order to offset temperatures necessary to process amounts of silicon dioxide.

For certain embodiments, the present composition also limits the amount of $SiO_2$ to no more than 15%, and in certain embodiments, to no more than 10%, as this amount provides long-term durability but does not substantially increase the processing temperature. For example, $SiO_2$ in the range of 20% or more increases the temperature required for processing the glass to the point where titanium, which can be used, for example, in conductive element 112, as part of a ferrule, or in the first substrate 111, undergoes a phase transition. This may cause titanium parts, or other metal parts approaching the respective metal or alloy melting temperature, to subsequently warp or become distorted. Thus, the present glass composition keeps the amount of silicon dioxide amount low to allow lower processing temperatures where integrity of titanium portion(s) of the feedthrough assembly 110 are maintained.

The present filled glass compositions also provide advantageous bonding and sealing between the insulating member 114 and the inner walls of aperture 106 and between the insulating member 114 and conductive element 112. In other embodiments, described below, the filled glass composition provides bonding and sealing to a ferrule. The present filled glass compositions may be used to replace glass insulating members used in feedthroughs as described in U.S. Pat. Nos. 6,855,456; 5,306,581; 5,175,067; and 4,940,858; and in U.S. Pat. App. Pub. No. 2006/0247714, all to Taylor et al., as well as U.S. Pat. No. 5,902,326 to Lessar et al.

Conductive element 112 and first substrate 111 are hermetically joined by the insulator material (e.g., glass) of insulating member 114 flowing and engaging conductive element 112 and the inner walls of aperture 106. The hermetic seal could be a coefficient of thermal expansion (CTE) value match, or an approximate match (e.g., CTE within 10%) for all MEMS package components. In another embodiment, the CTE may be within 5% for all MEMS package components. In another embodiment, the CTE may be within 2.5% for all MEMS package components. In yet another embodiment, first substrate 111 (e.g., housing) possesses a CTE greater than insulating member 114 and conductor 112, thereby forming a compression seal.

In a method of forming a feedthrough assembly 110, a glass preform may be positioned around a portion of an electrically conductive element 112. The glass preform may include the filled glass compositions as described herein. At least a portion of the glass preform may be positioned within an aperture 106 of a substrate 111 or within a sleeve member. The glass preform may be softened or fully melted to form a glass insulating member 114 having a sealing engagement with the electrically conductive element 112 and having a sealing engagement with the aperture 106 of the substrate 111 or the sleeve member. In some embodiments, softening or fully melting the glass preform to form a glass insulating member 114 having a sealing engagement with the electrically conductive element 112 and having a sealing engagement with the aperture 106 of the substrate 111 or the sleeve member does not require the use of one or more forming weights. In some embodiments, softening or fully melting the glass preform does not cause the electrically conductive element 112 to undergo a phase transition and does not cause the substrate 111 or the sleeve member to undergo a phase transition, preventing these components from becoming warped or distorted.

First substrate 111 includes a first surface 116a (also referred to as ceramic or glass housing material), a second surface 116b (e.g., silicon material), length X1, width X2, thickness X3, and an aperture 106 for receiving feedthrough assembly 110. First substrate 111 contains the hermetic seal feedthrough assembly 110 and metallized tracings for establishing an electrical connection to second substrate 128. In one embodiment, first substrate 111 includes a ceramic or glass having a coefficient thermal expansion (CTE) value equivalent to or greater than feedthrough 110 (e.g., pin/glass assembly).

In one embodiment, first substrate 111 may be included of a material that has an equivalent or greater CTE value than conductive element 112 and glass insulating member 114. First substrate 111 can include a ceramic such as for example, polycrystalline alumina with a CTE of 8.0, sapphire (e.g., single crystal alumina) with a CTE of 8.0, and zirconia with a CTE of 10. In another embodiment, first substrate 111 or housing may be made of glass instead of a ceramic, and possesses general characteristics such that (1) the glass has a higher melting point than insulating member 114; and/or (2) the glass has an equivalent or greater CTE value than the sealing glass.

Second substrate 128 includes via 122, a metallized trace 120 and includes electronic components that allow MEMS package 110 to function as a sensor substrate such as a transducer; however, skilled artisans appreciate that the substrate may be configured to include any type of circuitry such as switches, signal processing capability, and/or any other suitable form of circuitry related to an implantable medical devices. Second substrate 128 possesses about the same or similar dimensions as first substrate 111. For example, thickness X4 may be the same or about the same as X3. Wall thickness X5 forms a perimeter on the first surface 130 of second substrate 128. The second surface (not shown) of second substrate 128 may be directly adjacent to the housing of an implantable medical device.

Feedthrough assembly 110, disposed in first substrate 111, may then be coupled through joint 118 (e.g., a frit joint) to second substrate 128 (also referred to as a silicon MEMS substrate). Coupling of first substrate 111 to the second substrate 128 may be achieved by use of a glass frit, an Au-silicon eutectic material or other suitable material 118. Second substrate 128 (silicon) material generally has a higher melting point than the filled glass used to create to a glass insulating member 114. Conductive element 110 may be electrically connected to second substrate 128 through a metal tracing 120. In one embodiment, the metal tracing 120 may be located, for example, in second substrate 128.

Exemplary dimensions for components of MEMS package 100 include the following (however, skilled artisans appreciate that other dimensions may also be used): conductive element 112 diameter=0.40 millimeters (mm); glass insulating member 114 diameter=0.75 mm; length X1=3.50 mm; width X2=1.00 mm; thickness X3=0.40 mm; thickness X4=0.25 mm; wall X5=0.25 mm Skilled artisans understand other embodiments may implement the principles described herein. For example, a functional unit 20 may be placed in a free body such as a lead. Additionally, while MEMS package is described relative to a sensor or a sensor component (e.g., transducer), it is contemplated that MEMS package 100 can be used in a variety of ways to achieve certain functions of implantable medical devices.

Figure 3:
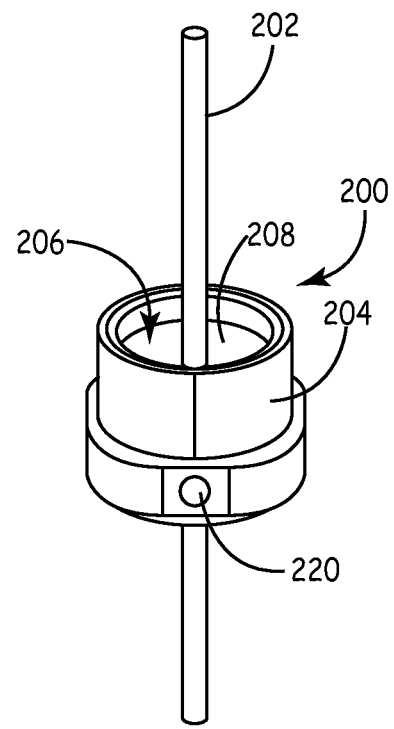
FIGS. 3 and 4 are isometric and cross-sectional views, respectively, of a unipolar (single pin) feedthrough assembly according to various embodiments of the present disclosure.
Figure 4:
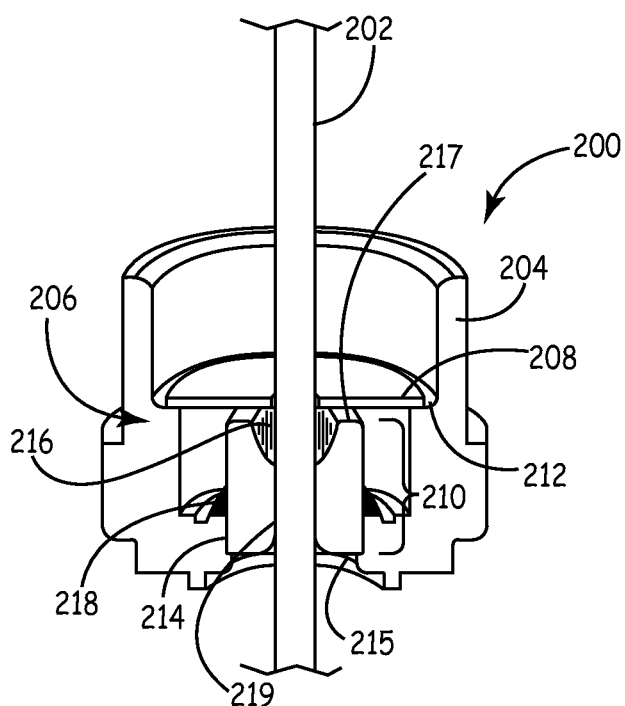

FIGS. 3 and 4 are isometric and cross-sectional views, respectively, of a unipolar (single pin) feedthrough assembly 200 having a terminal pin 202 extending therethrough. It should be understood, however, that the teachings of the present disclosure can be applied to feedthrough assemblies that include multiple terminal pins, as well as those that do not include terminal pins. Feedthrough assemblies that do not include terminal pins, such as those described in U.S. Pat. No. 5,902,326 (Lessar et al.), are sometimes referred to as "optical" feedthroughs.

Assembly 200 includes a generally cylindrical ferrule 204 having a cavity through which pin 202 passes. Ferrule 204 is made of an electrically conductive material (e.g., titanium alloy) and is configured to be fixedly coupled (e.g., welded) to the container of a device to be hermetically sealed, such as a medical device. An insulating structure 206 is disposed within ferrule 204 to secure pin 202 relative to ferrule 204 and to electrically isolate pin 202 from ferrule 204. Insulating structure 206 includes a supporting structure 208 and a joint-insulator sub-assembly 210, both of which are disposed around terminal pin 202. In various embodiments, supporting structure 208 may be absent from insulating structure 206. As will be more fully described below, joint-insulator sub-assembly 210 acts as an insulative seal and can take the form of, for example, a braze joint or glass seal (e.g., a filled glass seal, i.e., a glass seal that includes the filled glass described herein). Supporting structure 208 can be made of a non-conductive material (e.g., polyimide) and rests on an inner ledge 212 provided within ferrule 204.

As can be seen in FIG. 4, joint-insulator sub-assembly 210 includes three main components: an insulator ring 214 (e.g., made from a ceramic material) that insulates pin 202 from ferrule 204, a pin-insulator seal 216 (e.g., made from gold braze or glass seal) that couples insulating ring 214 to pin 202, and an insulator-ferrule seal 218 (e.g., made from gold braze or glass seal) that couples insulating ring 214 to ferrule 204. The insulator ring 214 can include a bottom portion 215, a top portion 217 and an inner diameter portion 219. The inner diameter portion 219 defines an aperture through which terminal pin 202 can extend.

In various embodiments of the present disclosure, one or both of the pin-insulator seal 216 and the insulator-ferrule seal 218 can be formed of the filled glass composition described above.

Joint-insulator sub-assembly 210 is exposed along the underside of ferrule 204. When ferrule 204 is fixedly coupled to the container of a medical device, for example, the bottom portion 215, and thus the lower portion of joint-insulator sub-assembly 210, can be exposed to body fluids. For this reason, it is important that joint-insulator sub-assembly 210 forms a hermetic seal between ferrule 204 and terminal pin 202. Joint-insulator sub-assembly 210 can be leak tested. To permit this test to be performed, an aperture 220 (FIG. 3) is provided through ferrule 204 to the inner annular cavity formed by the outer surface of joint-insulator sub-assembly 210, the lower surface of supporting structure 208, and the inner surface of ferrule 204. A gas is delivered through aperture 220 into the inner annular cavity, and aperture 220 is plugged. Preferably, a gas of low molecular weight (e.g., helium or hydrogen) is chosen so that it can easily penetrate small cracks in joint-insulator sub-assembly 210. This allows gas introduction to top portion 217 if otherwise blocked (e.g., due to a filter capacitor fully bonded to the pin and ferrule). Feedthrough 200 is then monitored for the presence of the gas proximate joint-insulator sub-assembly 210 by way of, for example, a mass spectrometer (e.g., at the bottom portion 215). If no gas is detected, it is concluded that joint-insulator sub-assembly 210 has formed a satisfactory seal.

Figure 5:
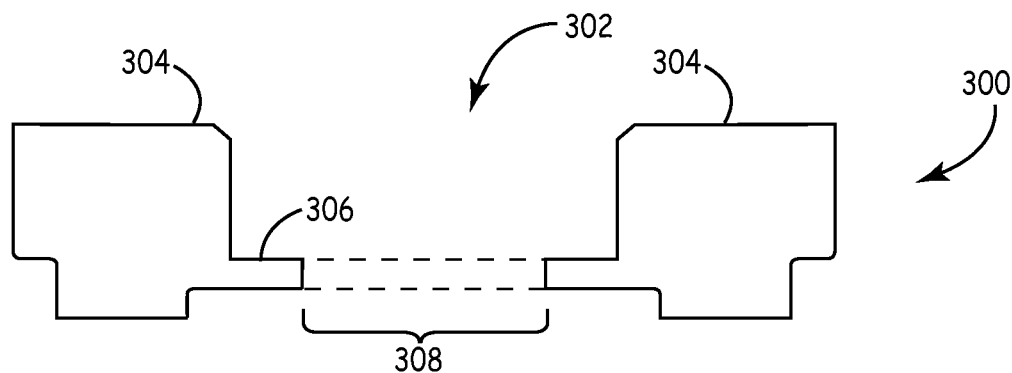
FIGS. 5-7 illustrate a method of manufacturing an exemplary feedthrough assembly according to various embodiments of the present disclosure.
Figure 6:
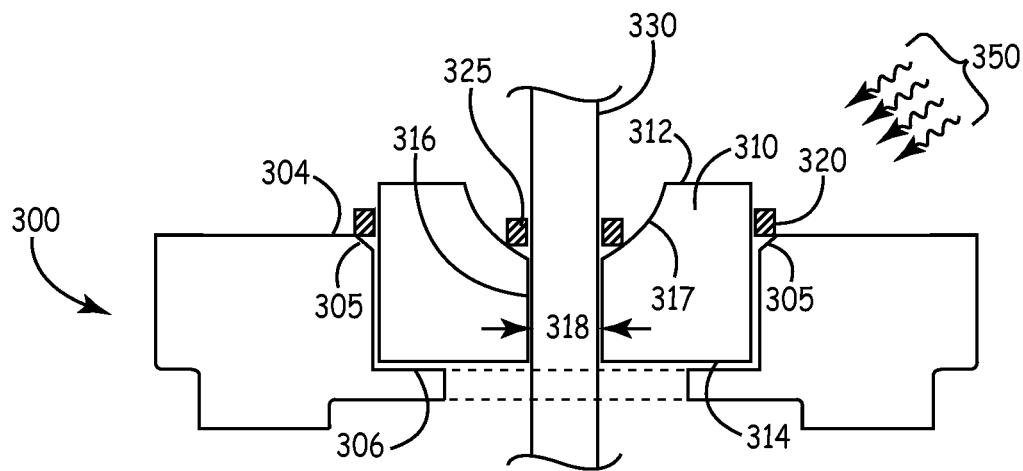
Figure 7:
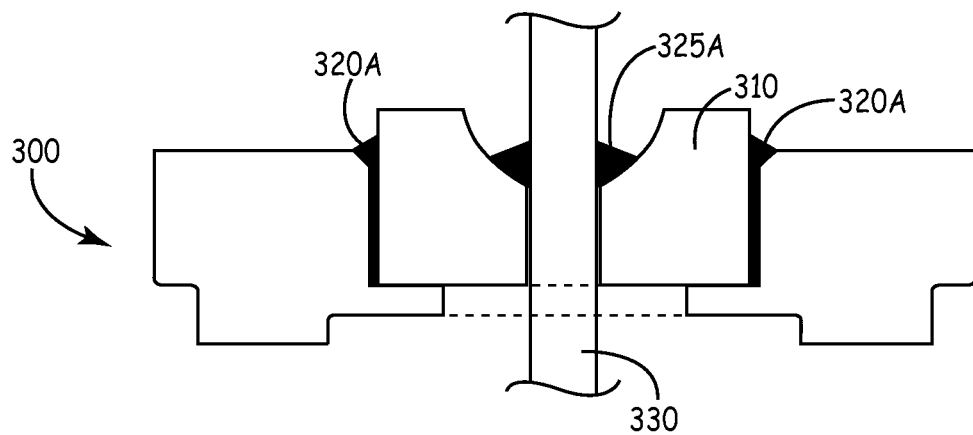

In reference to FIGS. 5-7, a method of manufacturing an exemplary feedthrough assembly is described. A ferrule 300 can include a recessed portion 302 in which an insulating structure 310 can be inserted. The recessed portion 302 can be bordered by wall portions 304 and further include a ledge 306 upon which an inserted insulating structure 310 can be placed such that the insulating structure 310 abuts the ledge 306. The recessed portion 302 can also define an opening 308 through which a terminal pin 330 can extend.

Insulating structure 310 can include a top portion 312, a bottom portion 314, and an inner diameter portion 316 that defines an aperture 318 that extends from the top portion 312 to the bottom portion 314. In various embodiments, insulating structure 310 can include an angled portion 317 that assists with the bonding of the terminal pin 330 with insulating structure 310, as described more fully below.

In various embodiments of the present disclosure, the insulating structure 310 is inserted into the recessed portion 302 and the terminal pin 330 is inserted into aperture 318. A glass preform 320 can be fitted around insulating structure 310, and a second glass preform 325 can be fitted around terminal pin 330. In various embodiments, a chamfer 305 can be included in wall portions 304 to more securely position the glass preform 320 adjacent insulating structure 310. Further, angled portion 317 can be included in the insulating structure to more securely position the glass preform 325 adjacent terminal pin 330.

Upon application of heat 350, glass preform 320 will soften or partially or completely melt and flow into the recessed portion 302 between insulating structure 310 and wall portions 304. In this manner, glass preform 320 will form a glass seal 320A that fixedly secures the insulating structure 310 to ferrule 300, as illustrated in FIG. 7. Different types of energy (e.g., radiation, microwave, magnetic) can be utilized instead of, or in addition to, heat 350, depending on the composition of the preform utilized. The same or similar method can be utilized to create glass seal 325A between terminal pin 330 and insulating structure 310. The use of one of glass seals 320A, 325A in combination with a gold braze or other sealing compositions (such as, glass seal 320A utilized with a gold braze utilized to seal terminal pin 330 with insulating structure 310, or glass seal 325A utilized with a gold braze utilized to seal ferrule 300 with insulating structure 310) is within the scope of the present disclosure.

In various embodiments of the present disclosure, the glass preforms 320, 325 and glass seals 320A, 325A can be formed of the filled glass composition described above.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, a feature of a medical device system as described herein may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The complete disclosures of the patents, patent documents, and publications cited herein are incorporated by reference in their entirety as if each were individually incorporated. To the extent that there is any conflict or discrepancy between this specification as written and the disclosure in any document that is incorporated by reference herein, this specification as written will control. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A method of forming a glass hermetic seal, the method comprising:
   forming a glass preform by:
   mixing a glass with a single-phase particulate to form a mixture, the glass having a first composition comprising:
   25% to 40% $B_2O_3$;
   0 to 25% CaO;
   0 to 25% MgO;
   0 to 25% SrO;
   0 to 10% $La_2O_3$;
   5% to 15% $SiO_2$;
   and 10% to 20% $Al_2O_3$ wherein all percentages are mole percentages of the glass powder;

forming a bulk shape from the mixture;

and heating the bulk shape to a reflow temperature above a glass transition temperature of the glass powder, wherein the glass preform comprises a continuous glassy matrix having the first composition with the single-phase particulate distributed throughout the glassy matrix, wherein the single-phase particulate has a second composition that is different from the first composition;

applying the glass preform between a conductive element and a substrate;

and applying heat to the glass preform to form the glass hermetic seal between the conductive element and substrate, wherein the glass hermetic seal does not include a glass ceramic.

2. The method of claim 1, wherein no reaction occurs between the glass powder and the single-phase particulate at the reflow temperature.

3. The method of claim 1, wherein the conductive element comprises tantalum (Ta), niobium (Nb), titanium (Ti), platinum (Pt), iridium (Ir), or an alloy thereof.

4. The method of claim 1, wherein the glass hermetic seal formed from the glass preform has a coefficient of thermal expansion that is within 15% of a coefficient of thermal expansion of the conductive element.

5. The method of claim 1, wherein the conductive element comprises niobium and the substrate comprises titanium.

6. The method of claim 1, wherein the applying heat to the glass preform to form the glass hermetic seal does not cause the conductive element or the substrate to undergo a phase transition.

7. The method of claim 1, wherein the mixture comprises 1 wt-% to 25 wt-% of the single-phase particulate based on the total weight of the glass and single-phase particulate.

8. The method of claim 1, wherein the glass powder comprises 30% $B_2O_3$, 5% $La_2O_3$, 10% $SiO_2$, 15% $Al_2O_3$, and 30% to 50% of a member selected from the group consisting of CaO, MgO, and combinations thereof, with the proviso that the individual amounts of CaO and MgO are each not greater than 25%.

9. The method of claim 1, wherein the single-phase particulate comprises $Al_2O_3$, $Y_2O_3$, $ZrO_2$, $TiO_2$, MgO, ZnO, BaO, CaO, $Nb_2O_5$, $Ta_2O_5$, SiC, $Si_3N_4$, or a combination thereof.

10. The method of claim 1, wherein the single-phase particulate has a particle size between 1 μm and 10 μm.

* * * * *